US00PP30049P3

(12) United States Plant Patent
Smith et al.

(10) Patent No.: US PP30,049 P3
(45) Date of Patent: Jan. 1, 2019

(54) ***DENDRANTHEMA* PLANT NAMED 'SUNDANCE IGLOO'**

(50) Latin Name: ***Chrysanthemum* X *morifolium***
Varietal Denomination: Sundance Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 34 days.

(21) Appl. No.: 15/530,072

(22) Filed: Nov. 30, 2016

(65) Prior Publication Data

US 2018/0153074 P1 May 31, 2018

(51) Int. Cl.
*A01H 5/02* (2018.01)

(52) U.S. Cl.
USPC ..... Plt./295
CPC ..... *A01H 5/02* (2013.01)

(58) Field of Classification Search
USPC ..... Plt./295
See application file for complete search history.

(56) References Cited

PUBLICATIONS

Aris Variety List, 2016.*

* cited by examiner

*Primary Examiner* — Keith O. Robinson
(74) *Attorney, Agent, or Firm* — C. A. Whealy

(57) ABSTRACT

A new and distinct cultivar of *Dendranthema* plant named 'Sundance Igloo', characterized by its upright, outwardly spreading and uniformly mounded plant habit; freely branching habit; dense and full plant form; uniform and freely flowering habit; daisy-type inflorescences; bright yellow-colored ray florets; natural season flowering occurs about September 14 to 24 in Pennsylvania; and good garden performance and winter hardiness.

2 Drawing Sheets

Botanical designation: *Chrysanthemum* X *morifolium*.
Cultivar denomination: 'SUNDANCE IGLOO'.

BACKGROUND OF THE INVENTION

The present invention relates to a new and distinct *Dendranthema* plant, botanically known as *Chrysanthemum* X *morifolium*, commercially grown as a perennial garden-type *Dendranthema* plant, and hereinafter referred to by the cultivar name 'Sundance Igloo'.

The new *Dendranthema* is the product of a planned breeding program conducted by the Inventors in Bogota, Colombia and Smoketown, Pa. The objective of the breeding program is to create new perennial garden-type *Dendranthema* plants having uniformly mounding plant habit, inflorescences with desirable inflorescence forms, attractive ray and disc floret shapes and colors, winter hardiness and good garden performance.

The new *Dendranthema* plant originated from a cross-pollination made by the Inventors in 2008 in Bogota, Colombia, of a proprietary seedling selection of *Chrysanthemum* X *morifolium* identified as code number N0012, not patented, as the female, or seed, parent with a proprietary selection of *Chrysanthemum* X *morifolium* identified as code number H5303, not patented, as the male, or pollen, parent. The new *Dendranthema* plant was discovered and selected by the Inventors as a single flowering plant within the progeny of the stated cross-pollination in a controlled greenhouse environment in Smoketown, Pa. on Sep. 29, 2010.

Asexual reproduction of the new *Dendranthema* plant by vegetative terminal cuttings was first conducted in a controlled greenhouse environment in Smoketown, Pa. in March, 2011 and such asexual propagation has shown that the unique features of this new *Dendranthema* plant are stable and reproduced true to type in successive generations.

SUMMARY OF THE INVENTION

Plants of the new *Dendranthema* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Sundance Igloo'. These characteristics in combination distinguish 'Sundance Igloo' as a new and distinct garden-type *Dendranthema* plant:

1. Upright, outwardly spreading and uniformly mounded plant habit.
2. Freely branching habit; dense and full plant form.
3. Uniform and freely flowering habit.
4. Daisy-type inflorescences.
5. Bright yellow-colored ray florets.
6. Natural season flowering occurs about September 14 to 24 in Pennsylvania.
7. Good garden performance and winter hardiness.

In side-by-side comparisons, plants of the new *Dendranthema* differ from plants of the female parent selection primarily in ray floret color as plants of the female parent selection have white-colored ray florets.

In side-by-side comparisons, plants of the new *Dendranthema* differ from plants of the male parent selection primarily in ray floret color as plants of the male parent selection have white-colored ray florets. In addition, plants of the new *Dendranthema* are larger and flower slightly earlier than plants of the male parent selection.

Plants of the new *Dendranthema* can be compared to plants of *Chrysanthemum* X *morifolium* 'Sizzling Igloo', disclosed in U.S. Plant Pat. No. 26,668. In side-by-side comparisons, plants of the new *Dendranthema* differ from plants of 'Sizzling Igloo' in the following characteristics:

1. Plants of the new *Dendranthema* are more compact than plants of 'Sizzling Igloo'.
2. Under low night temperatures conditions, plants of the new *Dendranthema* and 'Sizzling Igloo' differ in ray flower color as plants of 'Sizzling Igloo' will "pink" whereas plants of the new *Dendranthema* will retain their bright yellow ray floret coloration.

BRIEF DESCRIPTION OF THE PHOTOGRAPHS

The accompanying photographs illustrate the overall appearance of the new *Dendranthema* showing the colors as true as it is reasonably possible to obtain in colored reproductions of this type. Colors in the photographs may differ slightly from the color values cited in the detailed botanical description which accurately describe the colors of the new *Dendranthema* plant.

The photograph on the first sheet comprises a top perspective view of a typical flowering plant of 'Sundance Igloo' grown in a container.

The photograph on the second sheet is a close-up view of a typical flowering plant of 'Sundance Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type *Dendranthema* production. During the production of the plants, day temperatures averaged 26.7° C. and night temperatures ranged from 15.6° C. to 18.3° C. Plants were five months old when the photographs and description were taken. In the following description, color references are made to The Royal Horticultural Society Colour Chart, 2007 Edition, except where general terms of ordinary dictionary significance are used.

Botanical classification: *Chrysanthemum* X *morifolium* 'Sundance Igloo'.

Parentage:

*Female, or seed, parent*.—Proprietary selection of *Chrysanthemum* X *morifolium* identified as code number N0012, not patented.

*Male, or pollen, parent*.—Proprietary selection of *Chrysanthemum* X *morifolium* identified as code number H5303, not patented.

Propagation:

*Type*.—Vegetative terminal cuttings.

*Time to initiate roots, summer and winter*.—About two weeks.

*Root description*.—Fine, fibrous; typically white in color, actual color of the roots is dependent on substrate composition, water quality, fertilizer type and formulation, substrate temperature and physiological age of roots.

*Rooting habit*.—Freely branching, dense.

Plant description:

*Plant and growth habit*.—Perennial garden-type *Dendranthema* plant with daisy-type inflorescences; upright, outwardly spreading and uniformly mounding plant habit; strong and vigorous growth habit.

*Branching habit*.—Freely branching habit, primary lateral branches developing at potentially every node, each primary lateral with multiple secondary and tertiary branches; dense and full plant form; pinching is not required.

*Plant height*.—About 32 cm.

*Plant width*.—About 48 cm.

*Lateral branches*.—Length: About 35 cm. Diameter: About 5 mm. Internode length: About 1.5 cm. Strength: Strong. Aspect: Upright to curving upright. Texture: Pubescent, minute; longitudinally ridged. Color: Close to 144A.

*Leaves*.—Arrangement: Alternate, simple. Length: About 3.6 cm. Width: About 2.8 cm. Shape: Elliptical. Apex: Cuspidate to mucronate. Base: Truncate. Margin: Palmately lobed, sinuses between lateral lobes mostly parallel to slightly divergent and medium in depth. Texture and luster, upper and lower surfaces: Pubescent, minute; veins prominent on lower surface; matte. Venation pattern: Pinnate. Color: Developing and fully expanded leaves, upper surface: More green than 147A; venation, close to 147B. Developing and fully expanded leaves, lower surface: More green than 147B; venation, close to 146A. Petioles: Length: About 1 cm. Diameter: About 2 mm. Attitude: Slightly upright. Texture, upper and lower surfaces: Pubescent; minute. Color, upper surface: More green than 147A. Color, lower surface: More green than 147B.

Inflorescence description:

*Type and arrangement*.—Daisy-type inflorescence form with elongated oblong-shaped ray florets; disc and ray florets arranged acropetally on a capitulum; inflorescences face mostly upright and held above and beyond the foliar plane on strong peduncles.

*Fragrance*.—None detected.

*Flowering response*.—Under natural season conditions, plants flower about September 14 to 24 in Pennsylvania.

*Postproduction longevity*.—Inflorescences maintain good color and substance for about three to six weeks on the plant depending on temperatures; inflorescences persistent.

*Quantity of inflorescences*.—Freely flowering habit with inflorescences developing at every terminal.

*Inflorescence buds*.—Height: About 5 mm. Diameter: About 6 mm. Shape: Oblate. Color: More green than 147A.

*Inflorescence size*.—Diameter: About 3.6 cm. Depth (height): About 1.25 cm. Disc diameter: About 1 cm. Receptacle diameter: About 5 mm. Receptacle height: About 5 mm.

*Receptacle color*.—Close to 144A.

*Ray florets*.—Quantity and arrangement: About 32 to 45 ray florets develop per inflorescence and arranged in two to three whorls. Length: About 1.6 cm. Width: About 5 mm. Shape: Elongated oblong. Apex: Obtuse. Base: Attenuate and then fused into a short tube. Margin: Entire. Orientation: Initially upright, then horizontal. Texture, upper and lower surfaces: Smooth, glabrous; longitudinally ribbed. Color: When opening, upper surface: Close to 6A; at the base, close to 144A. When opening, lower surface: Close to 6A to 6B. Fully opened, upper surface: Close to 6A; at the base, close to 144A; color does not change with development. Fully opened, lower surface: Close to 6B to 6D; color does not change with development.

*Disc florets*.—Quantity and arrangement: About 32 to 48 fused disc florets develop per inflorescence and massed at the center of the capitulum. Length: About 5 mm. Diameter: About 1 mm. Shape: Tubular, elongated. Apex: Five-pointed. Texture, inner and outer surfaces: Smooth, glabrous. Color, mature: Apex: Close to 12A. Mid-section: Close to 144A. Base: Close to NN155D.

*Phyllaries*.—Quantity and arrangement: About 12 to 18 phyllaries develop per inflorescence and arranged in one to two whorls. Length: About 6.5 mm. Width: About 2 mm. Shape: Lanceolate. Apex: Acute. Base: Truncate. Margin: Entire; membraneous. Texture, upper surface: Smooth, glabrous. Texture, lower surface: Pubescent, minute. Color, upper surface: Close to 146A. Color, lower surface: More green than 147A.

*Peduncles*.—Length, terminal peduncle: About 4 cm. Length, third peduncle: About 5.5 cm. Diameter, terminal peduncle: About 2 mm. Angle: Mostly upright or curving upright. Strength: Strong, wiry. Texture: Pubescent; minute. Color: Close to 146A.

*Reproductive organs*.—Androecium (present on disc florets only): Stamen number: Five per floret. Filament length: About 4 mm. Filament color: Close to 150D. Anther length: Less than 1 mm. Anther shape: Narrowly oblong. Anther color: Close to 12A. Pollen amount: None observed. Gynoecium (present on ray and disc florets): Pistil length: About 6 mm. Stigma shape: Bi-parted. Stigma color: Close to 9A. Style length: About 4.5 mm. Style color: Close to 9A. Ovary color: Close to 145D.

*Seeds and fruits*.—Seed and fruit production has not been observed on plants of the new *Dendranthema*.

Disease & pest resistance: Resistance to pathogens and pests common to *Dendranthema* plants has not been observed on plants of the new *Dendranthema* grown under commercial production conditions.

Garden performance & temperature tolerance: Plants of the new *Dendranthema* have demonstrated excellent garden performance, are hardy to USDA Zone 5 and tolerate high temperatures about 37.8° C.

It is claimed:

1. A new and distinct *Dendranthema* plant named 'Sundance Igloo' as illustrated and described.

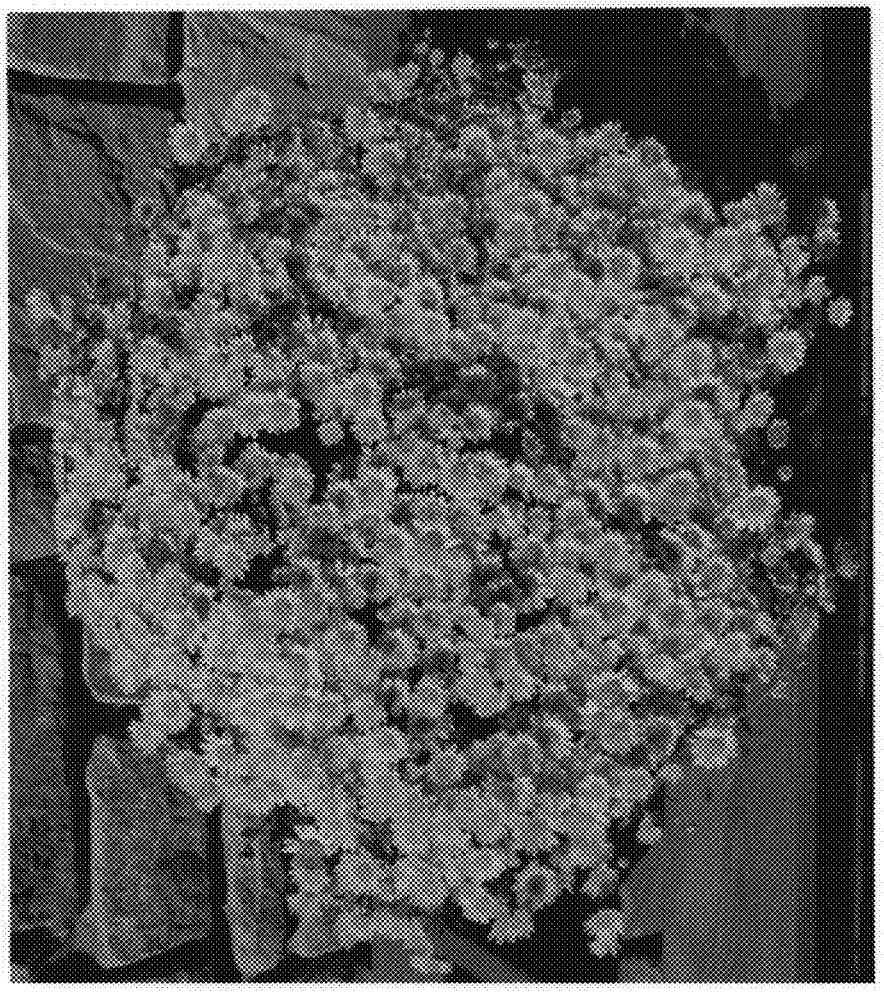

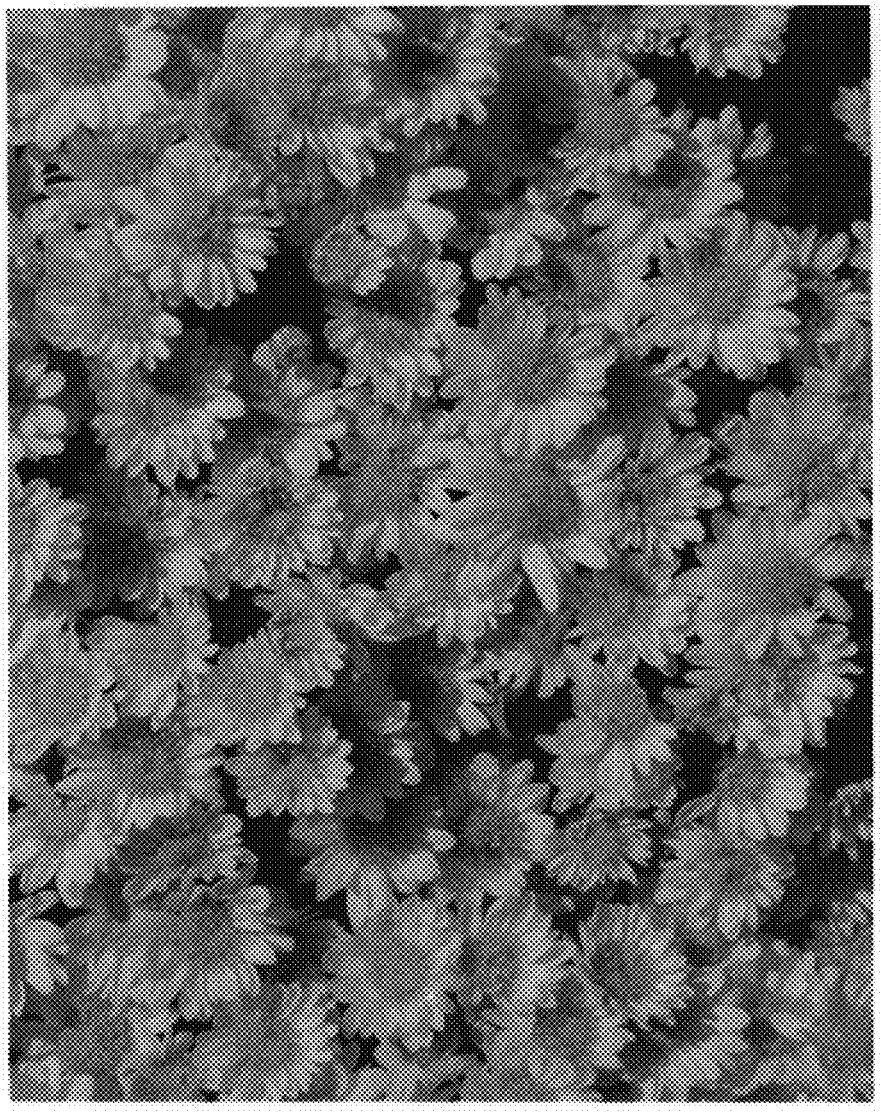

* * * * *